United States Patent [19]
Cohen et al.

[11] Patent Number: 4,891,436
[45] Date of Patent: Jan. 2, 1990

[54] PROCESS FOR PREPARING BIS-METHYLENE SPIROORTHOCARBONATE

[75] Inventors: Murray S. Cohen, Morristown; Morris Dunkel, Paramus, both of N.J.

[73] Assignee: Epolin, Inc., Newark, N.J.

[21] Appl. No.: 273,577

[22] Filed: Nov. 21, 1988

[51] Int. Cl.⁴ .......................................... C07D 319/04
[52] U.S. Cl. .................................. 549/335; 560/237; 556/89
[58] Field of Search ................ 549/335; 560/236, 237

[56] References Cited

U.S. PATENT DOCUMENTS 4,387,215 6/1983 Bailey ................................. 528/354
4,738,899 4/1988 Bluestein et al. ................... 428/413

OTHER PUBLICATIONS

Bailey et al., CA, 84(8): 44708a (1974).
Bailey et al., CA 87(12): 85280k (1976).
Mooradian & Clock JACS 67 042–943 (1945).

Primary Examiner—Nicky Chan
Attorney, Agent, or Firm—Albert L. Gazzola; Carl P. Steinhauser

[57] ABSTRACT

A process for the manufacture of bis-methylene spiro-orthocarbonate (BMSOC) wherein methyallyl chloride is subjected to the action of chlorine gas to form a mixture of 1,1-dichloromethyl ethylene and other chlorinated hydrocarbons which need not be and are not separated. The mixture is merely treated wich an alkali metal acetate such as sodium acetate to yield an easily separable second mixture by fractional distillation. The desired 1,1-diacetoxymethyl ethylene is thus recovered in high yield. It is then converted by transesterification in over 90% yield to the bismethylene spiroorthocarbonate (BMSOC). BMSOC is useful as a component for coatings composites, adhesive formulations and the like, which have the unique ability to (a) cure by free radical initiation and (b) expand during cure. BMSOC may be used as a component for dental composites, i.e. filling materials, because it reduces the possibility of leakage at the margin, i.e. at the composite-enamel interface and as a component in bone cements. It is also useful for the reduction of voids in electrical insulating coatings because it reduces the likelihood of corona and/or dielectric breakdown.

6 Claims, No Drawings

PROCESS FOR PREPARING BIS-METHYLENE SPIROORTHOCARBONATE

FIELD OF THE INVENTION

This invention relates to a commercially viable, relatively simple, inexpensive method of making bis-methylene spiroorthocarbonate (BMSOC) using readily available, inexpensive, starting materials and readily available reactants. Spiroorthocarbonates are useful in the manufacture of adhesives and coatings, as described in U.S. Pat. No. 4,738,899 to Bluestein and Cohen, in dental composites as filling materials, in bone cements and in electrical insulators for reducing electrical leakage and filling voids, as well as in many other applications which require good adhesion and low porosity.

BACKGROUND OF THE INVENTION

The manufacture of BMSOC has been described in detail in U.S. Pat. No. 4,387,215 to Bailey. As described in that patent, BMSOC is used in ring-opening polymerization.

Briefly, the process of Bailey may be described as follows. Dicyclopentadiene is heated to between 240°–250° C. to form an 80–85% yield cyclopentadiene, which is allowed to react with acrolein to produce norbornene carboxaldehyde in a yield of 79% based on the cyclopentadiene (83% based on the acrolein). The resulting norbornene carboxaldehyde is allowed to react with formaldehyde and caustic to form 5-norbornene-2,2-dimethanol which is heated to between 420°–450° C. to form 1,1-dihydroxymethyl ethylene and cyclopentadiene in a yield of 10–40%. The 1,1-dihydroxymethyl ethylene, is allowed to react with dibutyl tin oxide to form a cyclic tin intermediate which is allowed to react with carbon disulfide ($CS_2$) to form 3,9-dimethylene-1,5,7,11-tetraoxa-spiro[5,5]undecane (BMSOC).

Because the yield of the 1,1-dihydroxymethyl ethylene is so low and the pyrolysis procedure is difficult and costly on a commercial scale, and because dibutyl tin oxide is also costly, a new approach was sought. Furthermore, because Bailey's process uses acrolein which is toxic and has been declared too dangerous to ship and is mostly available only for captive use, this gave added impetus to seek a simpler, safer, less costly, more productive route to prepare BMSOC.

In search of this new process, it became evident that 1,1-dichloromethyl ethylene, already known from the literature, viz. Mooridian and Clarke, J.Am.Chem.Soc. 67, 942 (1945), would be a key intermediate in a process of manufacturing BMSOC. Unfortunately, the method of preparing 1,1-dichloromethyl ethylene described by Mooridian and Clarke involved a route which was expensive and inconvenient. Briefly, that method involved reacting pentaerythritol with thionyl chloride to form a mixture of chlorinated hydrocarbons and alcohols, one of which is trischloromethyl ethanol in a comparatively low yield. The trischloromethyl ethanol is oxidized with nitric acid to form trichloro-methyl acetic acid. The latter is converted at high temperature using quinoline to produce 1,1-dichloromethyl ethylene in low yield. This was then further converted to the corresponding diol, used by Bailey to make BMSOC. The diol was formed in very low yield by hydrolysis with lime.

OBJECTS OF THE PRESENT INVENTION

It is an object of the invention to provide a new, commercially viable and simpler process of preparing BMSOC using more readily available, inexpensive starting materials.

It is another object of the invention to provide a process of making BMSOC with an improved yield.

These and further objects of the invention will appear as the specification progresses.

SUMMARY OF THE INVENTION

A key starting material and component in the manufacture of adhesives and coatings as described in U.S. Pat. No. 4,738,899 to Bluestein and Cohen is a spiroorthocarbonate. The spiroorthocarbonates allow the cured composition to bond more strongly to surfaces and to reduce stresses and voids in the final cure. Furthermore, it would be desirable to use a monomer which can undergo cure at ordinary temperatures using free radical initiation. One such monomer, reported by Bailey, is bismethylene spiroorthocarbonate (BMSOC). To that end, it became of major importance to find a commercially viable method for making BMSOC at reasonable cost.

In one approach, the "bottoms" from the commercial production of methallyl chloride were used. These bottoms contain about 31.4% of 1,1-dichloromethyl ethylene after stripping a forecut. It was not necessary to separate the chlorinated hydrocarbon product which is a mixture of the desired 1,1-dichloromethyl ethylene with 1,3-dichloro-2-methyl propene-1 and 1,2,3-trichloro-2-methyl propane. Instead, to advantage, the mixture can be used in the next reaction as is.

Another approach is to chlorinate methallyl chloride to form 1,1-dichloromethyl ethylene in a 34 to 35% yield together with cis- and trans-1,3 dichloro-2-methyl propene-1 and 1,2,3-trichloro-2-methyl propane. This mixture of chlorinated hydrocarbons was treated, without separation, directly with an alkali metal carboxylate, such as sodium acetate or potassium acetate, to form an easily separated mixture. Surprisingly and to advantage the trichloro product does not react with the alkali metal carboxylate such as sodium acetate and can be separated by fractional distillation along with the other side products, leaving the desired diester(1,1-diacetoxymethyl ethylene) collected at 109°–112°/20 mm which was converted to the final product, bis-methylene spiroorthocarbonate (BMSOC) by transesterfication. Two routes of transesterfication are shown as follows:

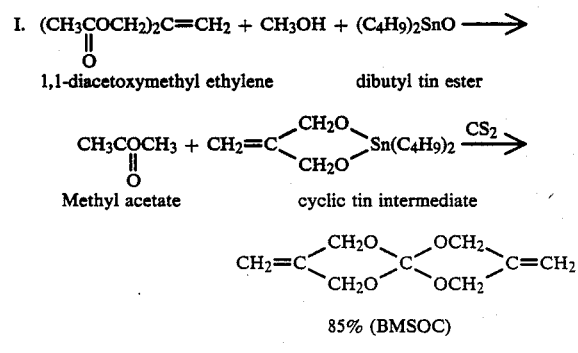

OR

-continued

II. $(CH_3COCH_2)_2C=CH_2 + (CH_3O)_4C \xrightarrow[\text{NaOMe or Bu}_2\text{SnO}]{\text{presence of catalyst}}$

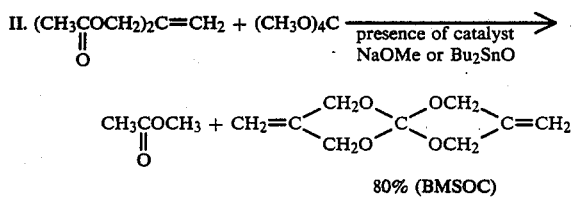

80% (BMSOC)

The tetramethyl orthocarbonate above may be replaced by other commercially available tetraalkyl orthocarbonates.

DETAILED DESCRIPTION

The invention will be described in connection with the following examples which, it will be understood, are representative only, and not limitative.

EXAMPLE 1

Use of Methallyl Chloride Bottoms

A mixture of bottoms from the commercial production of methallyl chloride from the FMC Corporation, which contains about 31.4% of 1,1-dichloromethyl ethylene after a forecut was stripped, weighed 37.5 Kg was placed in a 50 L flask set up with a distillation column and a fraction cutter. The low boiling fraction was separated which boiled up to about 116° C. This contained mostly isocrotyl chloride and 1,2-dichloro-2-methyl propane and weighed 22.4 Kg. The remainder of material was separated into four fractions as follows:

| Fraction | b.p. (°C.) | pressure (mm) | wt. (Kg) |
|---|---|---|---|
| 1 | 106–111 | 175 | 3.795 |
| 2 | 111–113 | 175 | 4.100 |
| 3 | 113–118 | 175 | 3.145 |
| 4 | pot residue | | 3.800 |

The individual fractions were analyzed for the desired product, 1,1-dichloromethylethylene, and the following concentrations were found.

| Fraction | % desired product |
|---|---|
| 1 | 38.6 |
| 2 | 45.4 |
| 3 | 42.5 |
| 4 | 10.0 (discarded) |

Fractions 1, 2 and 3 above were combined and used as in Example 3 below.

EXAMPLE 2

Chlorination of Methallyl Chloride 1.0 Kg of methallyl chloride was placed in a 2 L flask equipped with a gas delivery tube, a stirrer and a reflux condenser. The condenser exhaust was connected to a 10% sodium hydroxide scrubber to capture the effluent hydrogen chloride. The flask was cooled in a water bath and chlorine was introduced over a period of 5.0 hours. The temperature was maintained below 25° C. during the reaction. The apparatus was then set up for distillation. A forecut, b.p. 61°–118°, was collected that weighed 54 g. The remainder was not fractionated but used directly as in Example 3.

EXAMPLE 3

Preparation of 1,1-diacetoxymethyl-ethylene 522 g (bottoms) from Example 2 was diluted with 45 ml of toluene. Solid sodium acetate, 387.9 g, was added with stirring and then 9.5 g of tri-caprylmethyl ammonium chloride, a phase transfer agent. The reaction was mildly exothermic. It was heated to 130° C. and held there overnight. The gc showed complete reaction. Water, 750 ml, was added and two phases separated. The organic layer was washed with 200 ml of water and the organic layer was distilled.

| Fraction | b.p. (°C.) | pressure (mm) | composition | wt. (gm) |
|---|---|---|---|---|
| 1 | up to 45 | 40 | toluene +H$_2$O | 55 |
| 2 | 45 to 87 | 35 | trichloride | 91 |
| 3 | 87 to 91 | 40 | trichlor + chlorovinyl-ester | 126 |
| 4 | 88 to 89 | 35 | chlorovinyl-ester | 59 |
| 5 | 92 to 102 | 35 | same product | 14.8 |
| 6 | 109 to 112 | 20 | product | 200 |
| 7 | pot residue | | discard | 95 |

EXAMPLE 4

Preparation of BMSOC from 1,1-diacetoxymethylethylene and Dibutyl tin oxide

A 2.0 L 3-necked flask was equipped with thermometer, stirrer and a distillation column with a fraction cutter. This was charged with 258 g (1.5 mole) of 1,1-diacetoxymethylethylene, 400 g (1.61 mole) of dibutyltin oxide, 500 ml of toluene and 300 ml of methanol. After ½ hour of total reflux, methyl acetate was collected (b.p. 55°–57° C.). This is continued until the head temperature rises to 85° C. at which point the toluene water azeotrope is collected. The collection is continued for 6 hours until the head temperature reached the b.p. of toluene (111° C.). The clear solution of cyclic tin intermediate was then treated with 130 g (1.71 mole) of carbon disulfide. The solution was heated under total reflux for 5 hours and then the toluene was stripped in vacuo. The product was isolated by distilling it from the dibutyltin sulfide. The distillate crystallized as it was collected. Distillation was containued at 2 to 5 mm pressure until the pot temperature reaches 183° C. A total weight of 140 g of a wet solid is collected. This is redistilled to give a forecut of 15 g which consists of a mixture of starting diacetate and 1,1-dihydroxymethyl ethylene. The main fraction, 127 g (92%) is 98 to 99% pure BMSOC and has a boiling point of 100°–104° C. at 2.5 mm.

EXAMPLE 5

Preparation of BMSOC from 1,1-diacetoxymethylethylene and tetramethyl orthocarbonate A 500 ml 3-necked flask was fitted with a stirrer, thermometer and distillation column with a fraction cutter. The flask was charged with 63.2 g (0.36 mole) of 1,1-diacetoxymethyl ethylene, 25.0 g of tetramethyl orthocarbonate (0.18 mole), 100 ml toluene and 2.0 g of dibutyltin oxide. The mixture was heated to 55°–57° C. Methylacetate was slowly taken off over 4 hours. When the head temperature could no longer remain below 62°

C. the remaining toluene was removed in vacuo. The residue was distilled at 90°–110° C. at 2.5 mm pressure to give a wet solid which weighed 32 g. Redistillation gave a liquid forecut that was discarded and crystalline BMSOC which weighed 22.0 g (71%), b.p. 102°–104° C./2.5 mm.

While the invention has been described with reference to specific materials, reagents, and reaction conditions, it will be understood that these reactants and reaction conditions may be modified to suit the needs of the user without departing from the spirit and scope of the invention as defined in the appended claims.

We claim:

1. A process of preparing a spiroorthocarbonate comprising the steps of:
   (a) forming a mixture of chlorinated hydrocarbons, one of which is 1,1-dichloromethyl ethylene, from the chlorination of methallyl chloride;
   (b) treating the mixture in (a) above, with an alkali metal carboxylate and isolating the diester of 1,1-dihydroxy methyl ethylene by fractional distillation;
   (c) transesterifying the diester of 1,1-dihydroxy methyl ethylene to convert the same to bis-methylene spiroorthocarbonate.

2. A process as claimed in claim 1, wherein the mixture of chlorinated hydrocarbons is obtained after a forecut of the bottoms from the commercial production of methallyl chloride was stripped.

3. A process of preparing a spiroorthocarbonate comprising the steps of:
   (a) forming a mixture of chlorinated hydrocarbons by chlorinating methylallyl chloride;
   (b) subjecting the mixture of chlorinated hydrocarbons to the action of an alkali metal carboxylate to form a mixture of diester of 1,1-dihydroxymethyl ethylene and chlorinated by-products of lower boiling point;
   (c) separating the diester of 1,1-dihydroxymethyl ethylene from the lower boiling point chlorinated by-products; and
   (d) converting the diester of 1,1-dihydroxymethyl ethylene to bis-methylene spiroorthocarbonate by transesterification.

4. A process as claimed in claims 1 or 3 in which the diester of 1,1-dihydroxymethyl ethylene is transesterified using a dibutyl tin oxide, followed by treatment with carbon disulfide.

5. A process as claimed in claim 1 or 3 in which transesterification is by tetraalkyl orthocarbonate.

6. A process as claimed in claim 3 in which the alkali metal carboxylate is sodium acetate.

* * * * *